United States Patent [19]

Krenzer

[11] 4,255,182
[45] Mar. 10, 1981

[54] AMINOSULFONYLTHIADIAZOLYLUREAS

[75] Inventor: John Krenzer, Oak Park, Ill.

[73] Assignee: Velsicol Chemical Corporation, Chicago, Ill.

[21] Appl. No.: 128,774

[22] Filed: Mar. 10, 1980

[51] Int. Cl.³ .................. A01N 47/36; C07D 405/12; C07D 405/14

[52] U.S. Cl. .................. 71/90; 260/340.7; 260/340.9 R; 548/139; 548/140; 549/20

[58] Field of Search .............. 548/140; 546/209; 71/90

[56] References Cited

U.S. PATENT DOCUMENTS

| | | | |
|---|---|---|---|
| 3,726,892 | 4/1973 | Cebalo | 548/140 |
| 3,856,503 | 12/1974 | Cebalo | 548/140 |
| 3,901,902 | 8/1975 | Krenzer | 548/140 |
| 3,946,045 | 3/1976 | Richter et al. | 260/340.9 |
| 3,951,640 | 4/1976 | krenzer | 71/90 |
| 3,990,881 | 11/1976 | Cebalo | 548/140 |
| 4,012,222 | 3/1977 | Richter et al. | 71/88 |

Primary Examiner—Alton D. Rollins
Attorney, Agent, or Firm—Dietmar H. Olesch; Robert J. Schwarz

[57] ABSTRACT

Disclosed are compounds of the formula

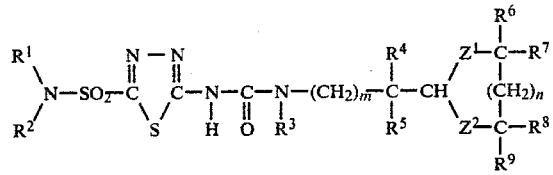

wherein $R^1$ is alkyl, $R^2$ is selected from the group consisting of hydrogen and alkyl; or $R^1$ and $R^2$ together with the nitrogen atom form a cyclic ring structure having 4 or 5 carbon atoms; m is the integer 0 or 1; when m is 1, $R^4$ and $R^5$ are each independently selected from the group consisting of hydrogen and alkyl or up to 3 carbon atoms; when m is 0, $R^4$ is hydrogen and $R^5$ is the same as defined above; $R^3$, $R^6$, $R^7$, $R^8$, $R^9$ are each independently selected from the group consisting of hydrogen and alkyl; n is an integer from 0 to 2; and $Z^1$ and $Z^2$ are each independently selected from the group consisting of oxygen and sulfur. These compounds are useful as herbicides.

10 Claims, No Drawings

AMINOSULFONYLTHIADIAZOLYLUREAS

This invention relates to new compositions of matter and more specifically relates to new chemical compounds of the formula

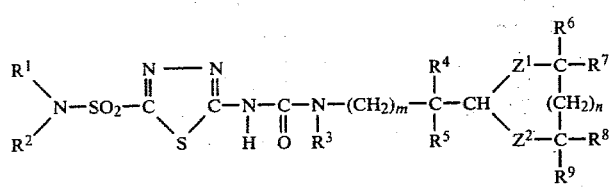
(I)

wherein $R^1$ is alkyl, $R^2$ is selected from the group consisting of hydrogen and alkyl; or $R^1$ and $R^2$ together with the nitrogen atom form a cyclic ring structure having 4 or 5 carbon atoms; m is the integer 0 or 1; when m is 1, $R^4$ and $R^5$ are each independently selected from the group consisting of hydrogen and alkyl of up to 3 carbon atoms; when m is 0, $R^4$ is hydrogen and $R^5$ is the same as defined above; $R^3$, $R^6$, $R^7$, $R^8$, $R^9$ are each independently selected from the group consisting of hydrogen and alkyl; n is an integer from 0 to 2; and $Z^1$ and $Z^2$ are each independently selected from the group consisting of oxygen and sulfur.

In a preferred embodiment of the present invention, $R^1$ is lower alkyl, $R^2$ is selected from the group consisting of hydrogen and lower alkyl, or $R^1$ and $R^2$ together with the nitrogen atom form a cyclic ring structure having 4 or 5 carbon atoms; m is the integer 0 or 1; when m is 1, $R^4$ and $R^5$ are each independently selected from the group consisting of hydrogen and alkyl of up to three carbon atoms; when m is 0, $R^4$ is hydrogen and $R^5$ is the same as defined above; $R^3$, $R^6$, $R^7$, $R^8$, and $R^9$, are each independently selected from the group consisting of hydrogen and lower alkyl; n is an integer from 0 to 2; and $Z^1$ and $Z^2$ are each independently selected from the group consisting of oxygen and sulfur.

The term "lower" as used herein designates a straight or branched carbon chain of up to 6 carbon atoms.

The compounds of this invention are useful as herbicides.

The compounds of this invention can be prepared by reacting a thiadiazolyl isocyanate dimer of the formula

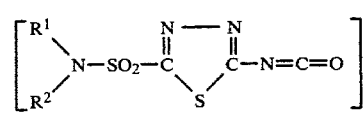
(II)

wherein $R^1$ and $R^2$ are as heretofore described, with a compound of the formula

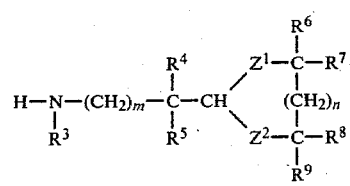
(III)

wherein $R^3$, $R^4$, $R^5$, $R^6$, $R^7$, $R^8$, $R^9$, m, $Z^1$, $Z^2$ and n are as heretofore described.

This reaction can be effected by adding the isocyanate dimer of formula II to a solution of the compound of formula III in an inert organic solvent such as ethyl acetate, chloroform or toluene at room temperature with stirring. The reaction mixture can then be heated on a steam bath for a period of from about 5 to about 180 minutes to ensure completion of the reaction. After this time the mixture can be stripped of solvent under reduced pressure to yield the desired product as a residue. This product can be used as such or can be further purified by conventional means.

The isocyanate dimer of formula II can be prepared by reacting an aminothiadiazole of the formula

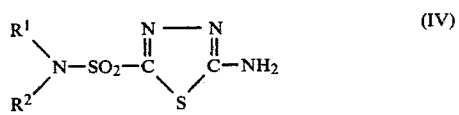
(IV)

wherein $R^1$ and $R^2$ are as heretofore described, with phosgene. This reaction can be effected by adding a solution of phosgene in ethyl acetate to a solution or suspension of the aminothiadiazole in ethyl acetate at room temperature with stirring. After the addition is completed stirring can be continued for a period of up to about 18 hours to ensure completion of the reaction. The reaction mixture can then be purged with nitrogen to remove unreacted phosgene. The desired product can then be recovered by filtration if it forms as a precipitate or upon evaporation of the solvents used if soluble therein.

Another method of preparing the isocyanate dimer of formula II is one similar to that reported by G. Westphal and P. Henklein, Z. Chem, 9 Jg. (1969) Heft 11, pp. 425, 426. Oxalyl chloride and the aminothiadiazole of formula IV can be reacted together in an inert reaction medium such as xylene or dichlorobenzene. The reactants are first held at a temperature of from about 80° C. to 100° C. for a period of from 1 to 2 hours. The reaction mixture is then brought to a temperature of from about 135° C. to about 180° C., and held at this temperature for a period of from 1 to 2 hours. Solvent is then removed to leave the desired product which can be used as such or can be further purified by standard means.

The compounds of formula IV can be prepared by the reaction sequence (A):

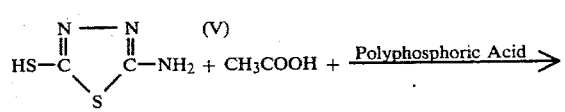
(V)

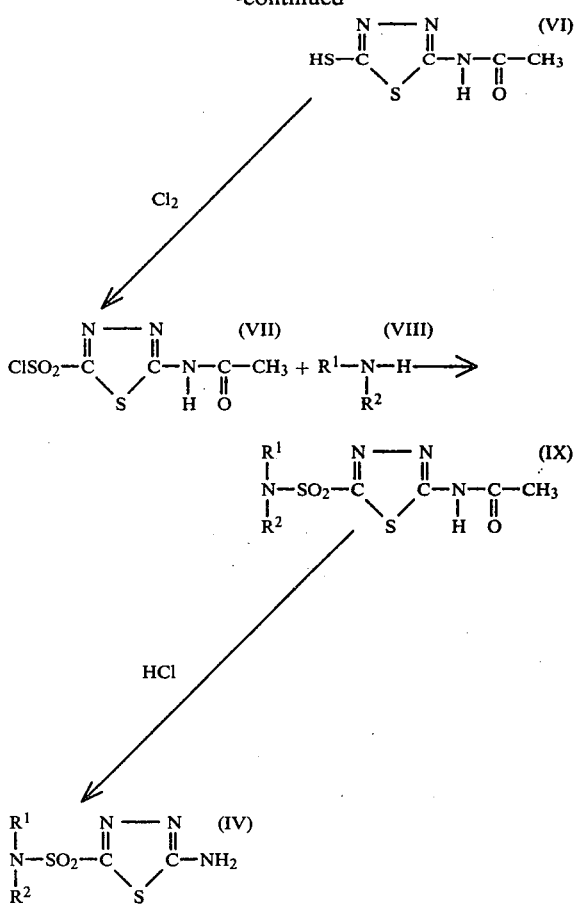

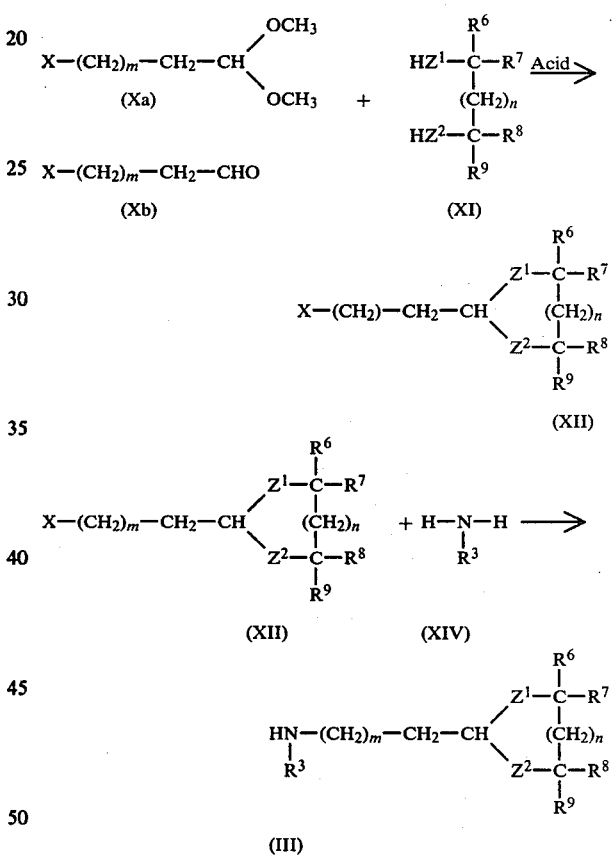

wherein $R^1$ and $R^2$ are as hereinbefore described. The aminomercaptothiadiazole of formula V can be esterified with acetic acid, in the presence of polyphosphoric acid to obtain the acetamido compound of formula VI. Approximately equimolar amounts of the thiadiazole of formula V and of polyphosphoric acid are used; a molar excess of acetic acid is preferable. The reactants are heated at a temperature of from about 110° C. to 125° C. for a period of from about 1 to 3 hours. The mixture is then cooled whereupon the desired product precipitates out and may be isolated and purified by conventional means. The chlorosulfonyl compound of formula VII can be prepared by suspending the acetamido compound of formula VI in a reaction medium such as a 70% aqueous solution of acetic acid, cooling to a temperature of from about −5° C. to 15° C. and bubbling chlorine gas through the suspension. The aminosulfonyl compound of formula IX can be prepared by reacting the compound of formula VII with amine of formula VIII. The reactants are stirred together, at room temperature, for a period of about 2 hours. Water can be used as the reaction medium when the amine of formula VIII is water soluble. Where the amine is water insoluble, inert organic solvents such as toluene, chloroform and the like can be used. At the conclusion of the reaction period, solvent and unreacted starting materials are removed to yield the desired product. Treating the compound of formula IX with concentrated hydrochloric acid yields the aminosulfonyl amino thiadiazole of formula IV. The compound of formula IX is refluxed with a molar excess of concentrated hydrochloric acid.

The aqueous acid is removed, the residue then is neutralized with a base such as sodium carbonate and, if desired, further purified by art-known methods.

The compounds of formula III can be prepared by various synthetic routes differing in the nature of the reactants and/or the reactions. The specific route chosen to make a compound of this invention is dependent on the value of m and the nature of the substituents $R^4$ and $R^5$. Three such routes are described below and are used to make compounds of formula III wherein ether: (1) m is 0 or 1 and $R^4$ and $R^5$ are both hydrogen; or (2) m is 0, $R^4$ is hydrogen and $R^5$ is alkyl of up to 3 carbon atoms; or (3) m is 1 and one or both of $R^4$ and $R^5$ is alkyl.

The compounds of formula III wherein m is 0 or 1 and both $R^4$ and $R^5$ are hydrogen can be prepared by the reaction sequence (B):

The symbols m, n, $R^3$, $R^6$, $R^7$, $R^8$, $R^9$, $Z^1$ and $Z^2$ have the meaning heretofore described, and X is chlorine or bromine. The reaction between the compounds of formula Xa and Xb and the compound of formula XI be effected by combining about equimolar amounts of these compounds, under anhydrous conditions, in the presence of an acid catalyst such as sulfuric acid or toluene sulfonic acid. The mixture can then be heated while removing the water or alcohol found in the reaction. When alcohol or water evolution ceases, the reactions mixture can be neutralized with base such as sodium carbonate or sodium hydroxide and then be distilled under reduced pressure to yield the compound of formula XII. This compound can then be reacted with an amine of formula XIII by combining the two compounds in a suitable solvent such as water or methanol.

The mixture can then be stirred at room temperature and atmospheric pressure for a period of up to about 18 hours. Preferably, however, the mixture is charged into a pressure vessel and agitated, at a temperature of from about 50° C. to about 110° C., under autogeneous pressure, for a period of from about 2 to about 20 hours. At the conclusion of the reaction period, the reaction mixture is neutralized with base such as sodium carbonate, sodium hydroxide, and the like. The product, the compound of formula III, can be isolated and purified by standard methods.

The compounds of formula III wherein m is 0 and $R^5$ is alkyl of up to 3 carbon atoms can be prepared by use of the above described reaction sequence (B) by substituting for the compound of formula X a compound of formula

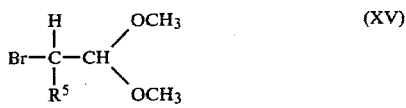

wherein $R^5$ has the heretofore described meaning. When not readily available, the compound of formula XV can be made by the reaction

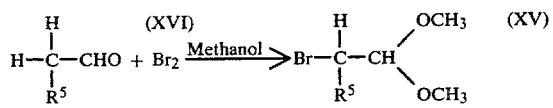

wherein $R^5$ is as heretofore described. The compound of formula XVI reacted with a molar excess of bromine in the presence of methanol. The reaction can be carried out in an inert reaction medium such as ethyl acetate, the reaction temperature is preferably held from about −10° C. to 10° C., and the duration of the reaction can be from 30 to 120 minutes. At the conclusion of this period, the reaction mixture is water washed, neutralized with base such as sodium carbonate or sodium bicarbonate, dried and the solvent and unreacted materials removed to yield the desired product.

The compound of formula III wherein m is 1 and one or both of $R^6$ and $R^5$ is alkyl can be prepared without the need for a reaction between an amine and a halocompound by use of a method similar to that reported by H. Mohrle and D. Schnadelbach (Archiv. der Pharmazie, 308, 352(1975). and 308, 783(1975). The reaction sequence used in (C):

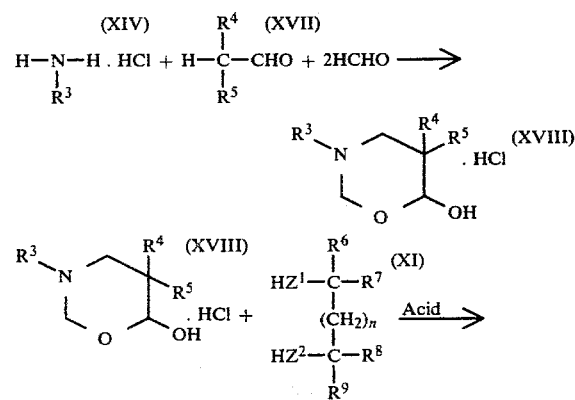

-continued

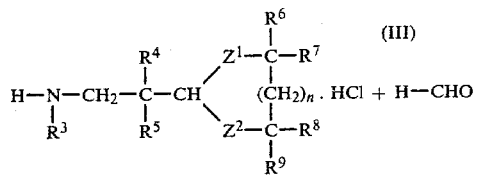

The symbols n, $R^3$, $R^4$, $R^5$, $R^6$, $R^7$, $R^8$, and $R^9$ have the same meaning as hereinbefore described. The compound of formula XVIII is prepared by combining the amine of formula XIV, in the form of its hydrochloride (the hydrochloride may be used as such or may be formed in situ from the amine by adding hydrochloric acid to the reaction medium), formaldehyde (either in aqueous solution or as paraformaldehyde) and the compound of formula XVII in an aqueous reaction medium. The reaction mixture is heated at reflux for a period of from 2 to 6 hours or until the mixture clears. Water is then removed, preferably by adding a water-immicable inert solvent such as toluene and azeotroping off the water leaving the compound of formula XVIII in solution. To this solution is then added the compound of formula XI together with a catalytic quantity of toluene solfonic acid. This reaction mixture is heated to reflux and water and volatiles distilled off. When water evolution ceases, the reaction mixture is cooled and neutralized with base such as sodium carbonate or sodium hydroxide to yield the compound of formula III This compound can be isolated and purified by standard techniques.

Exemplary amines of formula VIII suitable for preparing the compounds of this invention are N-methylethylamine, dimethylamine, diethylamine, dipropylamine, 1-pentylamine, 2-pentylamine, 3-hexylamine, dibutylamine, N-propylbutylamine, 1 H-pyrrol, pyrrolidine, piperidine and 1,2,3,6-tetrahydropyridine.

Exemplary alcohols and thiols of formula XI are 1,2-ethanediol; 1,2-propanediol; 1,3-propanediol; 1,2-butanediol; 1,3-butanediol; 1,4-butanediol; 2,3-butanediol; 1,2-pentanediol; 1,3-pentanediol; 1,4-pentanediol; 2,3-pentanediol; 2,4-pentanediol; 2-methyl-2,4-pentanediol; 1,2-dihexyl-1,2-ethanediol; 7,8-dipropyl-7,8-tetradecanediol; 4-butyl-4,6-dodecanediol; 3-propyl-6-butyl-3,6-octanediol; 1,2-hexanediol; 1,4-hexanediol; 2,4-hexanediol, 2,5-hexanediol; 3,4-hexanediol; 1,2-ethanedithiol; 1,2-propanedithiol; 1,3-propanedithiol; 1,2-butanedithiol; 1,3-butanedithiol; 1,4-butanedithiol; 2,4-dimethyl-4-mercapto-2-pentanol; 5-mercapto-3-hexanol; 5-mercapto-2-hexanol and the like.

The manner in which the compounds of this invention can be prepared is more specifically illustrated in the following examples. All temperature are in degrees Celsius and weights in grams unless otherwise indicated. Where a rotary evaporator is used to strip off volatiles, the conditions are: liquid temperature of from 40° C. to 80° C., pressure from 5 to 25 mm Hg.

EXAMPLE 1

Preparation of 2-acetamido-5-mercapto-1,3,4-thiadiazole

Polyphosphoric acid (190 grams) and acetic acid (406 grams) were charged into a glass reaction vessel fitted with a mechanical stirrer and thermometer and heated, with stirring, to 100° C. To this heated, stirred mixture was then added 2-amino-5-mercapto-1,3,4-thiadiazole (250 grams). Stirring was continued for an additional hour at a temperature of 120° C. The reaction mixture was then cooled to 60° C. and poured over ice. A precipitate formed which was filtered and air dried to yield the desired product 2-acetamido-5-mercapto-1,3,4-thiadiazole having a melting point greater than 290° C.

EXAMPLE 2

Preparation of 2-acetamido-5-chlorosulfonyl-1,3,4-thiadiazole

One liter of a 70% aqueous solution of acetic acid was charged into a glass reaction vessel fitted with a mechanical stirrer and thermometer. 2-Acetamido-5-mercapto-1,3,4-thiadiazole (250 mg) was added and kept in suspension by vigorous stirring. The suspension was cooled to a temperature of from 0° C. to 5° C. and held at this temperature while chlorine gas (300 grams) was slowly bubbled through it. Solids were filtered out, water washed and air dried to yield the desired product 2-acetamido-5-chlorsulfonyl-1,3,4-thiadiazole.

EXAMPLE 3

Preparation of 2-acetamido-5-(N,N-dimethylaminosulfonyl)-1,3,4-thiadiazole

A 40% aqueous solution of dimethylamine (400 ml) was charged into a glass reaction vessel fitted with a mechanical stirrer and thermometer. The solution was cooled to 20° C. and stirred while 2-acetamido-5-chlorosulfonyl-1,3,4-thiadiazole (250 grams) was slowly added. Ther temperature of the reaction mixture was kept between 0° and 20° C. during this addition. Stirring was then continued at room temperature for a period of about 2 hours. The reaction mixture was then treated with 6N hydrochloric acid. Solids were filtered out, water washed and air dried to yield the desired product 2-acetamido-5-(N,N-dimethylaminosulfonyl)-1,3,4-thiadiazole.

EXAMPLE 4

Preparation of 2-amino-5-(N,N-dimethylaminosulfonyl)-1,3,4-thiadiazole

2-Acetamido-5-(N,N-dimethylaminosulfonyl)-1,3,4-thiadiazole (250 grams) and concentrated hydrochloric acid (1 L) were charged into a glass reaction vessel fitted with a mechanical stirrer, reflux condenser and thermometer. This mixture was refluxed for a period of about 2 hours. It was then cooled to room temperature, filtered and the solvent stripped from the filtrate using a rotary evaporator. The solid residue was washed with 10% aqueous sodium carbonate (200 ml), air dried, then crystallized from isopropanol. These crystals were the desired product 2-amino-5-(N,N-dimethylaminosulfonyl)-1,3,4-thiadiazole and having a melting point of 188°-190° C.

EXAMPLE 5

Preparation of 5-(N,N-dimethylaminosulfonyl)-1,3,4-thiadiazol-2-yl isocyanate dimer 2-amino-5-(N,N-dimethylaminosulfonyl)-1,3,4-thiadiazole (42 grams) and xylene (300 ml) were charged into a glass reaction vessel fitted with a mechanical stirrer, thermometer and condenser. The mixture was dried by azeotroping off water and was then cooled to room temperature. Oxalyl chloride (25 grams) was then added. The reaction was warmed to a temperature of from about 80°-100° C. and stirred at this temperature for a period of about 1 hour. The mixture was then heated to reflux and stirred for an additional 2 hours. Solvent was then stripped off leaving the desired product 5-(N,N-dimethylaminosulfonyl)-1,3,4-thiadiazol-2-yl isocyanate dimer as the residue. Melting point: 253°-256° C. (decomposition).

EXAMPLE 6

Preparation of 2-chloromethyl-1,3-dioxolane

2-Chloro-1,1-dimethoxyethane (0.1 mole) and ethylene glycol (0.1 mole) are charged into a glass reaction vessel fitted with a mechanical stirrer, thermometer, Dean Stark trap and reflux condenser. Toluene sulfonic acid (0.1 grams) is added and the reaction mixture is heated and alcohol removed. When alcohol evolution ceases, the reaction mixture is then cooled to room temperature, treated with sodium carbonate (5 grams) and filtered. Volatiles are stripped from the filtrate using a rotary evaporator to yield the desired product 2-chloromethyl-1,3-dioxolane as the residue.

EXAMPLE 7

Preparation of N-(1,3-dioxolan-2-ylmethyl)methylamine

2-Chloromethyl-1,3-dioxolane (60 grams) and 40% aqueous methylamine (160 ml) are charged into a pressure vessel and heated, with agitation, at a temperature of about 100° C. for a period of about 16 hours under autogeneous pressure. At the end of this period, the reaction mixture is cooled to room temperature and 16 grams of sodium hydroxide are added. The resulting mixture is extracted with methylene chloride. The extract is dried, then stripped of solvent to yield the desired product N-(1,3-dioxolan-2-ylmethyl)methylamine.

EXAMPLE 8

Preparation of N-[5-(N,N-dimethyaminosulfonyl)-1,3,4-thiadiazol-2-yl]-N'-(1,3-dioxolan-2-ylmethyl)-N'-methylurea 5-(N,N-Dimethylaminosulfonyl)-1,3,4-thiadiazol-2-yl isocyanate dimer (6 grams), N-(1,3-dioxolan-2-ylmethyl)-N-methylamine (6 grams) and ethyl acetate (20 ml) were charged into a glass reaction vessel fitted with a mechanical stirrer. The reaction mixture was heated on a steam bath for a period of about 2 hours. Solvent was then stripped off using a rotary evaporator to yield the desired product N-[5-(N,N-dimethylaminosulfonyl)-1,3,4-thiadiazol-2-yl]-N'-(1,3-dioxolan-2-ylmethyl)-N'-methylurea as the residue. Melting point 100°-110° C.

EXAMPLE 9

Preparation of 2-ethyl-1,3-dioxolane

Propionaldehyde (180 grams), ethylene glycol (180 grams) hexane (300 ml) and toluene sulfonic acid (0.1 grams) were charged into a glass reaction vessel fitted with a mechanical stirrer, thermometer, Dean-Start trap and condenser. The reaction mixture was heated to reflux and water was azeotroped off. The heating was continued until water evolution ceased. The reaction mixture was cooled to room temperature, treated with sodium carbonate (2 grams) and filtered. Solvent was stripped from the filtrate using a rotary evaporator. The residue was then distilled at atmospheric pressure to yield the desired product 2-ethyl-1,3-dioxolane as a fraction boiling at 103°–104° C.

EXAMPLE 10

Preparation of 2-(1-bromoethyl)-1,3-dioxolane

2-Ethyl-1,3-dioxolane (75 grams) pentane (200 ml) and sodium carbonate (40 grams) were charged into a glass reaction vessel fitted with a mechanical stirrer and thermometer. The mixture was cooled to a temperature of about 5° C. and bromine (115 grams) was added slowly while holding the temperature at about 5° C. Stirring was continued overnight at room temperature. The reaction mixture was then filtered and volatiles removed leaving the desired product 2-(1-bromoethyl)-1,3-dioxolane as the residue.

EXAMPLE 11

Preparation of N-[1-(1,3-dioxolan-2-yl)ethyl]methylamine 2-(1-Bromoethyl)-1,3-dioxolane (60 grams) and 40% aqueous methylamine (160 ml) were charged into a pressure vessel and heated, with agitation, for a period of about 16 hours at a temperature of about 100° C. under autogeneous pressure. At the end of this period, the reaction mixture was cooled to room temperature and 16 grams of NaOH added. The resulting mixture was then extracted with methylene chloride. The extract was dried, then stripped of methylene chloride by use of a rotary evaporator. The residue was distilled to yield the desired product N-[1-(1,3-dioxolan-2-yl)ethyl]methylamine as a fraction boiling at 60° C.–65° C. at about 12 mm Hg pressure.

EXAMPLE 12

Preparation of N-[5-(N,N-dimethylaminosulfonyl)-1,3,4-thiadiazol-2-yl]-N'-[1-(1,3-dioxolan-2-yl)ethyl]-N'-methylurea N-[2-(1,3-dioxolan-2-yl)ethyl]methylamine (2 grams), 5-(N,N-dimethylaminosulfonyl)-1,3,4-thiadiazol-2-yl isocyanate dimer (2 grams) and chloroform (10 ml) were charged into a glass reaction vessel fitted with a mechanical stirrer and thermometer. The reaction mixture was warmed on a steam bath for a period of about 2 hours. The reaction mixture was then cooled to room temperature and filtered. Solvent was stripped from the filtrate using a rotary evaporator. The residue was dissolved in warm ethyl acetate, the desired product N-[5-(N,N-dimethylaminosulfonyl)-1,3,4-thiadiazol-2-yl]-N'-[1-(1,3-dioxolan-2-yl)ethyl]-N'-methylurea crystalize out as a solid with melting point 194° C.–196° C. Elemental analysis:

EXAMPLE 13

Preparation of 2-bromomethyl-4,5-dimethyl-1,3-dioxolane

2-Bromo-1,1-dimethoxyethane (188 grams) 2,3-butanediol (100 grams) and toluene sulfonic acid (0.1 grams) were charged into a glass reaction vessel fitted with a mechanical stirrer, thermometer, and reflux condenser. The reaction mixture was heated to reflux for a period of about 2 hours. It was then cooled to room temperature, neutralized with potassium carbonate, and filtered. The filtrate was distilled, the desired product 2-bromomethyl-4,5-dimethyl-1,3-dioxolane being obtained as a fraction boiling at 82° C.–85° C. at a pressure of about 12 mm Hg.

EXAMPLE 14

Preparation of N-(4,5-dimethyl-1,3-dioxolan-2-ylmethyl)methylamine

2-Bromomethyl-4,5-dimethyl-1,3-dioxolane (100 grams) and 40% aqueous methylamine (300 ml) were charged into a glass reaction vessel fitted with a mechanical stirrer and thermometer and were stirred at room temperature for a period of about 14 hours. The reaction mixture was then extracted with diethyl ether. The extract was dried and the ether stripped off using a rotary evaporator to yield the desired product N-(4,5-dimethyl-1,3-dioxolan-2-ylmethyl)methylamine as the residue.

EXAMPLE 15

Preparation of N-[5-(N,N-dimethylaminosulfonyl)-1,3,4-thiadiazol-2-yl]-N'-(4,5-dimethyl-1,3-dioxolan-2-ylmethyl)-N'-methylurea N,N-Dimethylaminosulfonyl-1,3,4-thiadiazol-2-yl isocyanate dimer (5 grams), N-(4,5-dimethyl-1,3-dioxolan-2-ylmethyl)methylamine (5 grams), and chloroform (20 ml) were charged into a glass reaction vessel fitted with a mechanical stirrer and thermometer. The reaction mixture was heated on a steam bath for a period of about 2 hours. Solvent was then stripped using a rotary evaporator. The residue was redissolved in acetone, treated with activated carbon, filtered and the acetone stripped from the filtrate. This residue was redissolved in ethyl acetate, treated with fullers earth, filtered and cooled. The desired product N-[5-(N,N-dimethylaminosulfonyl-1,3,4-thiadiazol-2-yl]-N'-(4,5-dimethyl-1,3-dioxolan-2-ylmethyl)-N'-methylurea crystallized out. Melting point 133°–134° C.

EXAMPLE 16

Preparation of 2-bromomethyl-4-methyl-1,3-dioxane

2-Bromo-1,1-dimethoxyethane (0.1 mole) and 1,3-butanediol (0.1 mole) are charged into a glass reaction vessel fitted with a mechanical stirrer, thermometer, Dean Stark trap and reflux condenser. Toluene sulfonic acid (0.1 grams) is added and the reaction mixture is heated and alcohol removed. When alcohol evolution ceases, the reaction mixture is then cooled to room temperature, treated with sodium carbonate (5 grams) and filtered. Volatiles are stripped from the filtrate using a rotary evaporator to yield the desired product 2-bromomethyl-4-methyl-1,3-dioxane as the residue.

EXAMPLE 17

Preparation of N-(4-methyl-1,3-dioxan-2-ylmethyl)methylamine 2-bromomethyl-4-methyl-1,3-dioxane (160 grams) and 40% aqueous methylamine (150 ml) were charged into a pressure vessel and agitated for a period of about 6 hours at a temperature of about 50° C. under autogeneous pressure. The reaction mixture was cooled to room temperature and sodium hydroxide (40 grams) was added. The reaction mixture was then extracted with methylene chloride. The extract was dried and the methylene chloride stripped off using a rotary evaporator to yield the desired product N-(4-methyl-1,3-dioxan-2-ylmethyl)methylamine.

EXAMPLE 18

Preparation of
N-[5-(N,N-dimethylaminosulfonyl)-1,3,4-thiadiazol-2-yl]-N'-(4-methyl-1,3-dioxan-2-ylmethyl)-N'-methylurea N-(4-methyl-1,3-dioxan-2-ylmethyl)-methylamine (6 grams), 5-(N,N-dimethylaminosulfonyl)-1,3,4-thiadiazol-2-yl isocyanate dimer (6 grams) and chloroform (20 ml) were charged into a glass reaction vessel and stirred at room temperature for a period of about 2 hours. The solvent was then stripped off on a rotary evaporator and the residue treated with a mixture of diethyl ethyl (100 ml)/water (50 ml). The ether, layer was isolated and dried. Ether was stripped off an a rotary evaporator to yield the desired product N-[5-(N,N-dimethylaminosulfonyl)-1,3,4-thiadiazol-2-yl]-N'-(4-methyl-1,3-dioxan-2-ylmethyl)-N'-methylurea as the residue. Melting point 131° C.–133° C.

EXAMPLE 19

Preparation of
N-[2,2-dimethyl-2-(1,3-dioxolan-2-yl)ethyl]methylamine

Methylamine hydrochloride (115 grams), paraformaldehyde (90 grams), 2-methylpropionaldehyde (150 ml) and water (100 ml) were charged into a glass reaction vessel fitted with a mechanical stirrer, thermometer and reflux condenser. The reaction mixture was stirred and refluxed until it became clear. Toluene (500 ml) was added and water was azeotroped off. Ethylene glycol (200 ml) and toluene sulfonic acid (0.1 grams) were then added to the vessel and heating and azeotroping was continued until water evolution ceased. The reaction mixture was then cooled to room temperature and, while holding the reaction temperature in the range 0° C. to 20° C., 50% aqueous sodium hydroxide (150 grams) was added. The organic layer was then isolated, dried and distilled. The desired product N-[2,2-dimethyl-2-(1,3-dioxolan-2-yl)ethyl]methylamine was obtained as fraction boiling at 58° C.–62° C. at 1 mm Hg.

EXAMPLE 20

Preparation of
N-[5-(N,N-dimethylaminosulfonyl)-1,3,4-thiadiazol-2-yl]-N'-[2,2-dimethyl-2-(1,3-dioxolan-2-yl)ethyl]-N'-methylurea 5-(N,N-Dimethylaminosulfonyl)-1,3,4-thiadiazol-2-yl isocyanate dimer (6 grams), N-[2,2-dimethyl-2-(1,3-dioxolan-2-yl)methylamine (6 grams) and ethyl acetate (20 ml) are charged into a glass reaction vessel fitted with a mechanical stirrer. The reaction mixture is heated on a steam bath for a period of about 2 hours. Solvent is then stripped off using a rotary evaporator to yield the desired product N-[5-(N,N-dimethylaminosulfonyl)-1,3,4-thiadiazol-2-yl]-N'-[2,2-dimethyl-2-(1,3-dioxolan-2-yl)ethyl]-N'-methylurea as the residue.

EXAMPLE 21

Preparation of
N-[2,2-dimethyl-2-(4-methyl-1,3-dioxolan-2-yl)ethyl]methylamine

Forty percent aqueous methylamine (150 ml), concentrated hydrochloric acid (140 ml), paraformaldehyde (90 grams) and 2-methylpropionaldehyde (150 ml) were charged into a glass reaction vessel fitted with a mechanical stirrer, thermometer and reflux condenser. The reaction mixture was stirred and refluxed until it became clear. Toluene (500 ml) was added and water was azeotroped off. 1,2-Propanediol (200 ml) and toluene sulfonic acid (0.1 grams) were then added to the vessel and heating and azeotroping was continued until water evolution ceased. The reaction mixture was then cooled to room temperature and, while holding the reaction temperature in the range 0° C. to 20° C., 50% aqueous sodium hydroxide (150 grams) was added. The organic layer was then isolated, dried and the desired product N-[2,2-dimethyl-2-(4-methyl-1,3-dioxolan-2-yl)ethyl]methylamine distilled off as a fraction boiling at 45° C.–48° C. at 0.2 mm Hg.

EXAMPLE 22

Preparation of
N-[5-(N,N-dimethylaminosulfonyl)-1,3,4-thiadiazol-2-yl]-N'-[2,2-dimethyl-2-(4-methyl-1,3-dioxolan-2-yl)ethyl]-N'-methylurea 5-(N,N-Dimethylaminosulfonyl)-1,3,4-thiadiazol-2-yl isocynate dimer (6 grams) N-[2,2-dimethyl-2-(4-methyl-1,3-dioxolan-2-yl)ethyl]methylamine (6 grams) and ethyl acetate (20 ml) are charged into a glass reaction vessel fitted with a mechanical stirrer. The reaction mixture is heated on a steam bath for a period of about 2 hours. Solvent is then stripped off using a rotary evaporator to yield the desired product N-[5-(N,N-dimethylaminosulfonyl)-1,3,4-thiadiazol-2-yl]-N'-[2,2-dimethyl-2-(4-methyl-1,3-dioxolan-2-yl)ethyl]-N'-methylurea as the residue.

EXAMPLE 23

Preparation of
N-[2,2-dimethyl-2-(4-methyl-1,3-dioxan-2-yl)ethyl]methylamine

Forty percent aqueous methylamine (150 ml), concentrated hydrochloric acid (140 ml), paraformaldehyde (90 grams) and 2-methylpropionaldehyde (150 ml) were charged into a glass reaction vessel fitted with a mechanical stirrer, thermometer and reflux condenser. The reaction mixture was stirred and refluxed until it became clear. Toluene (500 ml) was added and water was azeotroped off. 1,3-Butanediol (200 ml) and toluene sulfonic acid (0.1 grams) were then added to the vessel and heating and azeotroping continued until water evolution ceased. The reaction mixture was then cooled to room temperature and, while holding the reaction temperature in the range 0° C. to 20° C., 50% aqueous sodium hydroxide was added. The organic layer was isolated, dried, and the desired product N-[2,2-dimethyl-2-(4-methyl-1,3-dioxan-2-yl)ethyl]methylamine distilled off as fraction boiling at 54°–56° C. at 0.2 mm Hg.

EXAMPLE 24

Preparation of
N-[5-(N,N-dimethylaminosulfonyl)-1,3,4-thiadiazol-2-yl]-N'-[2,2-dimethyl-2-(4-methyl-1,3-dioxan-2-yl)ethyl]-N'-methylurea 5-(N,N-Dimethylaminosulfonyl)-1,3,4-thiadiazol-2-yl isocyanate dimer (6 grams) N-[2,2-dimethyl-2-(4-methyl-1,3-dioxan-2-yl)ethyl]methylamine (6 grams) and ethyl acetate (20 ml) are charged into a glass reaction vessel fitted with a mechanical stirrer. The reaction mixture is heated on a steam bath for a period of about 2 hours. Solvent is then stripped off using a rotary evaporator to yield the desired product N-[5-(N,N-dimethylaminosulfonyl)-1,3,4-thiadiazol-2-yl]-N-[2,2- dimethyl-2-(4-methyl-1,3-dioxan-2-yl)ethyl]-N-methylurea as the residue.

EXAMPLE 25

Preparation of
2-acetamido-5-[N-(1-ethylpropyl)aminosulfonyl]-1,3,4-thiadiazole

1-Ethylpropylamine (0.1 mole) and water (50 ml) are charged into a glass reaction vessel fitted with a mechanical stirrer and thermometer. The solution is cooled to 20° C. and stirred while 2-acetamido-5-chlorosulfonyl-1,3,4-thiadiazole (0.1 mole) is added slowly while holding the reaction temperature between 0° C. and 20° C. At the conclusion of the addition, stirring is continued for a period of about 2 hours at room temperature. The reaction mixture is then neutralized with 6 N hydrochloric acid. Solids are filtered out, water washed and dried to yield the desired product 2-acetamido-5-[N-(1-ethylpropyl)aminosulfonyl]-1,3,4-thiadiazole.

EXAMPLE 26

Preparation of
2-amino-5-[N-(1-ethylpropyl)aminosulfonyl]-1,3,4-thiadiazole

2-Acetamido-5-[N-(1-ethylpropyl)aminosulfonyl]-1,3,4-thiadiazole (0.1 mole), and concentrated hydrochloric acid (500 ml) are charged into a glass reaction vessel fitted with a mechanical stirrer, thermometer and reflux condenser. The mixture is refluxed for a period of about 2 hours, it is then cooled to room temperature, filtered and solvent removed from the filtrate by use of a rotary evaporator. The solid residue is washed with, 10% aqueous sodium carbonate, air dried and then crystallized from isopropanol to yield the desired product 2-amino-5-[N-(1-ethylpropyl)aminosulfonyl]-1,3,4-thiadiazole.

EXAMPLE 27

Preparation of
5-[N-(1-ethylpropyl)aminosulfonyl]-1,3,4-thiadiazol-2-yl isocyanate dimer 2-Amino-5-[N-(1-ethylpropyl)aminosulfonyl]-1,3,4-thiadiazole (0.10 mole) and xylene (200 ml) are charged into a glass reaction vessel fitted with a mechanical stirrer, thermometer and condenser. The mixture is dried by azeotroping off water and is then cooled to room temperature. Oxalyl chloride (0.15 mole) is added; the reaction mixture is warmed to a temperature of from 80° C. to about 100° C. and stirred at this temperature for a period of about 1 hour. The mixture is then heated to reflux and stirred for an additional 2 hours. Solvent is then stripped off leaving the desired product 5-[N-(1-ethylpropyl)aminosulfonyl]-1,3,4-thiadiazol-2-yl isocyanate dimer as the residue.

EXAMPLE 28

Preparation of
2-chloromethyl-4,4,6,6-tetramethyl-1,3-dithiane

2-Chloro-1,1-dimethoxyethane (0.1 mole) and 2,4-dimethyl-2,4-pentanedithiol (0.1 mole) are charged into a glass reaction vessel fitted with a mechanical stirrer, thermometer, Dean Stark trap and reflux condenser. Toluene sulfonic acid (0.1 grams) is added and the reaction mixture is heated and thiol removed. When the thiol evolution ceases, the reaction mixture is then cooled to room temperature, treated with sodium carbonate (5 grams) and filtered. Volatiles are stripped from the filtrate using a rotary evaporator to yield the desired product 2-chloromethyl-4,4,6,6-tetramethyl-1,3-dithiane as the residue.

EXAMPLE 29

Preparation of
N-(4,4,6,6-tetramethyl-1,3-dithian-2-ylmethyl)methylamine

2-Chloromethyl-4,4,6,6-tetramethyl-1,3-dithiane (60 grams) and 40% aqueous methylamine (160 ml) are charged into a pressure vessel and heated, with agitation, at a temperature of about 100° C. for a period of about 16 hours under autogeneous pressure. At the end of this period, the reaction mixture is cooled to room temperature and 16 grams of sodium hydroxide are added. The resulting mixture is extracted with methylene chloride. The extract is dried, then stripped of solvent to yield the desired product N-(4,4,6,6-tetramethyl-1,3-dithian-2-ylmethyl)methylamine.

Additional compounds within the scope of the present invention can be prepared by the procedures detailed in the foregoing examples. In the following examples are given the essential starting materials to prepare the indicated named compounds by the methods heretofore described.

EXAMPLE 30

5-[N-(1-ethylpropylaminosulfonyl)]-1,3,4-thiadiazol-2-yl isocyanate dimer+N-(4,4,6,6-tetramethyl -1,3-dithian-2-ylmethyl)methylamine+N-[5-(1-ethylpropylaminosulfonyl)-1,3,4-thiadiazol-2-yl]-N'-(4,4,6,6-tetramethyl-1,3-dithian-2-ylmethyl)-N'-methylamine.

EXAMPLE 31

5-(N,N-dimethylaminosulfonyl)-1,3,4-thiadiazol-2-yl isocyanate dimer+N-(4,4,6,6-tetramethyl-1,3-dithian-2-ylmethyl)-N-methylamine=N-[5-(N,N-dimethylaminosulfonyl)-1,3,4-thiadiazol-2-yl]-N'-(4,4,6,6-tetramethyl-1,3-dithian-2-ylmethyl)-N'-methylurea.

EXAMPLE 32

5-(N,N-dimethylaminosulfonyl)-1,3,4-thiadiazol-2-yl isocanate dimer+N-methyl-N-(1,3-dioxan-2-ylmethyl)amine=N-[5-(N,N-dimethylaminosulfonyl)-1,3,4-thiadiazol-2-yl]-N'-(1,3-dioxan-2-ylmethyl)-N'-methylurea; melt point 173° to 176° C.

Addition compounds within the scope of the present invention which can be prepared by the procedures of the foregoing examples are further exemplified by the following: N-[5-(1-pyrrolysulfonyl)-1,3,4-thiadiazol-2-yl]-N'-[2-(1,3-dixoepan-2-yl)ethyl]-N'-methylurea; N-[5-(1-piperidinylsulfonyl)-1,3,4-thiadiazol-2-yl]-N'-[1-(1,3-dithiepan-2-yl)ethyl]-N'-ethylurea; N-[5-(N-methylaminosulfonyl)-1,3,4-thiadiazol-2-yl]-N'-[2-ethyl-2-(1,3-oxathiolan-2-yl)ethyl]-N'-methylurea; N-[5-(N,N-dipropylaminosulfonyl)-1,3,4-thiadiazol-2-yl]-N'-(4,6-dimethyl-1,3-dioxan-2-ylmethyl)-N-'-ethylurea; N-[5-(N-ethylaminosulfonyl)-1,3,4-thiadiazol-2-yl]-N'-[2-(4-propyl-1,3-dithiolan-2-yl)ethyl]-N'-propylurea; N-[5-(N,N-dibuthylaminosulfonyl)-1,3,4-thiadiazol-2-yl]-N'-[2,2-dipropyl-2-(1,3-oxathian-2-yl)ethyl]-N'-butylurea; N-[5-(N-pentylaminosulfonyl)-1,3,4-thiadiazol-2-yl]-N'-(4,4-dimethyl-1,3,-oxathiepan-2-ylmethyl)-N'-hexylurea and the like.

For practical use as herbicides, the compounds of this invention are generally incorporated into herbicidal composition which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under superatmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems, an inverted emulsion (water in oil) can be prepared for direct application to weed infestation.

A typical herbicidal composition according to this invention is illustrated by the following example, in which the quantities are in parts by weight.

EXAMPLE 33

Preparation of a Dust

Product of Example 8–10
Powdered Talc—90

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to 95 percent by weight of the active compounds of this invention. In a preferred embodiment of this invention, the herbicidal compositions will comprise from about 5 to 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 2,4-DB, 2,4-DEB, 4-CPB, 4-CPA, 4-CPP, 2,4,5-TB, 2,4,5-TES, 3,4-DA, silvex and the like, carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron linuron, monolinuron, neburon, buturon, trimeturon and the like; symmetrical triazine herbicides such as simazine, chlorazine, atraone, desmetryne, norazine, ipazine, prometryn, atrazine, trietazine, simetone, prometone, propazine, ametryne, and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl) morpholine, 1-(chloracetyl) piperidine, and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, pichloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambs-quarters, foxtail, crabgrass, wild mustard, field pennycress, ryegrass, goose-grass, chickweed, wild oats, velvet leaf, purselane, barnyard grass, smartweed, knotweed, cocklebur, wild buckwheat, kochia, medic, corn cockle, ragweed, sow-thistle, coffee-weed croton, cuphea, dodder, fumitory, groundsel, hemp nettle, knowel, spurg, spurry, emex, jungle rice, pondweed, dog fennel, carpetweed, morningglory, bedstraw, ducksalad and naiad; biennials such as wild carrot, matricaria, wild barley, campion, chamomile, burdock, mullein, roundleaved mallow, bull thistle, hounds-tongue moth mullein, and purple star thistle; or perennials such as white cockle, perennial rye-grass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail and winter-cress.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively non-toxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention was demonstrated by experiments carried out for the pre-emergence control of a variety of weeds. In these experiments small plastic greenhouse pots filled with dry soil were seeded with the various weed seeds. Twenty-four hours or less after seeding, the pots were sprayed with water until the soil was wet and the test compounds dissolved in a solvent comprising a mixture of 45 volumes acetone, 2 volumes methanol and one volume N,N-dimethyl formamide were sprayed at the indicated concentrations on the surface of the soil.

After spraying, the soil containers were placed in the greenhouse and provided with supplementary heat as required and daily or more frequent watering. The plants were maintained under these conditions for a period of from 14 to 21 days, at which time the condition of the plants and the degree of injury to the plants was rated on a scale of from 0 to 10, as follows: 0=no injury, 1,2=slight injury, 3,4=moderate injury, 5,6=moderately severe injury, 7,8,9=severe injury and 10=death. N.E. indicates no emergence of the plant from the soil and values in parenthesis represent replicate experiments. The effectiveness of these compounds is demonstrated by the data in Tables I to V below.

The herbicidal activity of the compounds of this invention was also demonstrated by experiments carried out for the post-emergence control of a variety of weeds. In these experiments the compounds to be tested were formulated as aqueous emulsions and sprayed at the indicated dosage on the foliage of the weeds that have attained a prescribed size. After spraying, the plants were placed in a greenhouse and watered daily or more frequently. Water was not applied to the foliage of the treated plants. The severity of the injury was determined 14 days after treatment and was rated on the scale of from 0 to 10 heretofore described. The effectiveness of these compounds is demonstrated by the data in Tables VI to X below.

TABLE I

Product of Example 8 Pre-Emergence Injury Rating

| Plant Species | Rate Lbs./Acre | | | | | | |
|---|---|---|---|---|---|---|---|
| | 8 | 4 | 2 | 1 | 0.5 | 0.25 | 0.125 |
| YNSG | 4 | 2 | 0 | 0 | — | — | — |
| WOAT | 10 | 10 | 10 | 10(10)* | 10 | 6 | 3 |
| JMWD | 7 | 10 | 9 | 9(10) | 10 | 0 | 0 |
| VTLF | 10 | 10 | 10 | 10(10) | 4 | 0 | 0 |
| JNGS | 10 | 10 | 10 | 10(10) | 5 | 3 | 0 |
| PIGW | 4 | 10 | 10 | (9)10 | 7 | 6 | 10 |
| WHST | 10 | 10 | 10 | 3(4) | 1 | 0 | 0 |
| YLFX | 7 | 10 | 7 | 7(5) | 2 | 0 | 0 |
| BNGS | 10 | 10 | 10 | 10(10) | 4 | 0 | 0 |
| CBGS | 6 | 9 | 9 | 8(9) | 6 | 3 | 2 |
| CTGS | NE | 10 | 10 | 9(10) | 10 | 0 | 0 |
| MNGY | 10 | 10 | 10 | 8(10) | 2 | 0 | 0 |
| BDWD | — | — | — | 10 | 10 | 6 | 7 |
| QKGS | — | — | — | 10 | 10 | 10 | 2 |
| SPGT | — | — | — | 10 | 2 | 2 | 0 |
| SUBT | — | — | — | 10 | 10 | 10 | 9 |
| WHT | — | — | — | 10 | 10 | 10 | 0 |
| RICE | — | — | — | 10 | 7 | 4 | 0 |
| SOYB | — | — | — | 10 | 10 | 3 | 0 |
| COTN | — | — | — | 10 | 3 | 0 | 0 |
| SORG | — | — | — | 10 | 10 | 6 | 0 |
| PTBN | — | — | — | 10 | 10 | 7 | 3 |
| CORN | — | — | — | 10 | 3 | 0 | 0 |
| ALFA | — | — | — | 10 | 10 | 6 | 0 |
| OAT | — | — | — | 10 | 10 | 10 | 3 |

*values in parenthesis are replicate experiments

TABLE II

Product of Example 12 Pre-Emergence Injury Rating

| Plant Species | Rate Lbs./Acre | | | | | | |
|---|---|---|---|---|---|---|---|
| | 8 | 4 | 2 | 1 | 0.5 | 0.25 | 0.125 |
| YNGS | 5 | 2 | 1 | 1 | — | — | — |
| WOAT | 10 | 10 | 10 | 10(10) | 8 | 10 | 3 |
| JMWD | 10 | 10 | 10 | 6(10) | 10 | 10 | 2 |
| VTLF | 8 | 10 | 10 | 10(10) | 5 | 3 | 0 |
| JNGS | 10 | 9 | 8 | 8(10) | 6 | 5 | 3 |
| PIGW | 10 | 10 | 10 | 10(10) | 10 | 9 | 0 |
| WHST | 10 | 10 | 10 | 10(10) | 10 | 8 | 7 |
| YLFX | 8 | 8 | 8 | 8(10) | 5 | 0 | 0 |
| BNGS | 10 | 10 | 9 | 9(6) | 0 | 0 | 0 |
| CBGS | 7 | 9 | 8 | 0(7) | 5 | 0 | 0 |
| CTGS | 4 | 10 | 10 | 6(10) | 5 | 0 | 0 |
| MNGY | 10 | 9 | 10 | 9(10) | 10 | 6 | 4 |
| BDWD | — | — | — | 3 | 2 | 0 | 0 |
| QKGS | — | — | — | 10 | 10 | 10 | 0 |
| SPGT | — | — | — | 7 | 0 | 0 | 0 |
| SUBT | — | — | — | 10 | 10 | 10 | 10 |
| WHT | — | — | — | 10 | 10 | 10 | 5 |
| RICE | — | — | — | 10 | 10 | 3 | 2 |
| SOYB | — | — | — | 10 | 7 | 5 | 3 |
| COTN | — | — | — | 10 | 6 | 0 | 0 |
| SORG | — | — | — | 9 | 6 | 3 | 2 |
| PTBN | — | — | — | 10 | 10 | 10 | 2 |

TABLE II-continued

Product of Example 12 Pre-Emergence Injury Rating

| Plant Species | Rate Lbs./Acre | | | | | | |
|---|---|---|---|---|---|---|---|
| | 8 | 4 | 2 | 1 | 0.5 | 0.25 | 0.125 |
| CORN | — | — | — | 10 | 3 | 2 | 2 |
| ALFA | — | — | — | 2 | 2 | 10 | 0 |
| OAT | — | — | — | 10 | 10 | 10 | 3 |

TABLE III

Product of Example 15 Pre-Emergence Injury Rating

| Plant Species | Rate Lbs./Acre | | | | | | |
|---|---|---|---|---|---|---|---|
| | 8 | 4 | 2 | 1 | 0.5 | 0.25 | 0.125 |
| YNSG | 10 | 5 | 1 | 0 | — | — | — |
| WOAT | 10 | 10 | 10 | 10(10) | 10 | 9 | 7 |
| JMWD | 10 | 10 | 10 | 3(10) | 4 | 3 | |
| VTLF | 9 | 10 | 10 | 10(10) | 3 | 0 | 0 |
| JNGS | 10 | 10 | 9 | 10(10) | 10 | 6 | 4 |
| PIGW | 9 | 10 | 10 | 10(10) | 10 | 4 | 0 |
| WHST | 10 | 10 | 10 | 10(10) | 10 | 8 | 5 |
| YLFX | 10 | 8 | 8 | 3(9) | 9 | 0 | 0 |
| BNGS | 10 | 10 | 10 | 9(7) | 3 | 4 | 4 |
| CBGS | 8 | 9 | 4 | 1(9) | 4 | 0 | 0 |
| CTGS | 10 | 9 | 10 | 3(9) | 10 | 7 | 2 |
| MNGY | 10 | 10 | 10 | 2(10) | 10 | 8 | 4 |
| BDWD | — | — | — | 10 | 4 | 0 | 0 |
| QKGS | — | — | — | 10 | 10 | 10 | 10 |
| SPGT | — | — | — | 9 | 3 | 0 | 0 |
| SUBT | — | — | — | 10 | 10 | 10 | 10 |
| WHT | — | — | — | 10 | 10 | 10 | 7 |
| RICE | — | — | — | 10 | 10 | 4 | 3 |
| SOYB | — | — | — | 10 | 10 | 0 | 0 |
| COTN | — | — | — | 10 | 3 | 0 | 0 |
| SORG | — | — | — | 10 | 10 | 4 | 2 |
| PTBN | — | — | — | 10 | 10 | 5 | 2 |
| CORN | — | — | — | 7 | 3 | 1 | 2 |
| ALFA | — | — | — | 7 | 0 | 0 | 0 |
| OAT | — | — | — | 10 | 10 | 10 | 7 |

TABLE IV

Product of Example 18 Pre-Emergence Injury Rating

| Plant Species | Rate Lbs./Acre | | | | | | |
|---|---|---|---|---|---|---|---|
| | 8 | 4 | 2 | 1 | 0.5 | 0.25 | 0.125 |
| YNSG | 6 | 0 | NE | 3 | — | — | — |
| WOAT | 10 | 10 | 10 | 10(10) | 7 | 5 | 2 |
| JMWD | 10 | 10 | 10 | 9(10) | 8 | 5 | 2 |
| VTLF | 10 | 10 | 9 | 10(7) | 4 | 0 | 0 |
| JNGS | 8 | 10 | 10 | 10(9) | 5 | 2 | 0 |
| PIGW | 10 | 10 | 10 | 10(9) | 8 | 7 | 7 |
| WHST | 10 | 10 | 10 | 10(10) | 10 | 10 | 3 |
| YLFX | 10 | 8 | 9 | 5(9) | 4 | 1 | 0 |
| BNGS | 10 | 8 | 10 | 6(5) | 3 | 2 | 0 |
| CBGS | 8 | 9 | 9 | 3(9) | 6 | 0 | 0 |
| CTGS | 10 | 9 | 10 | 9(8) | 10 | 4 | 0 |
| MNGY | 10 | 10 | 9 | 10(9) | 9 | 5 | 4 |
| BDWD | — | — | — | 3 | 0 | 0 | 0 |
| QKGS | — | — | — | 10 | 10 | 9 | 0 |
| SPGT | — | — | — | 10 | 2 | 0 | 0 |
| SUBT | — | — | — | 10 | 10 | 10 | 10 |
| WHT | — | — | — | 10 | 10 | 7 | 0 |
| RICE | — | — | — | 7 | 4 | 1 | 0 |
| SOYB | — | — | — | 10 | 10 | 10 | 0 |
| COTN | — | — | — | 0 | 0 | 0 | 0 |
| SORG | — | — | — | 10 | 4 | 2 | 0 |
| PTBN | — | — | — | 10 | 10 | 10 | 6 |
| CORN | — | — | — | 6 | 0 | 0 | 0 |
| ALFA | — | — | — | 7 | 7 | 0 | 0 |
| OAT | — | — | — | 10 | 10 | 10 | 2 |

TABLE V

Product of Example 32 Pre-Emergence Injury Rating

| Plant Species | Rate Lbs./Acre | | | |
|---|---|---|---|---|
| | 8 | 4 | 2 | 1 |
| YNSG | 1 | 0 | 0 | 0 |
| WOAT | 10 | 10 | 10 | 6 |
| JMWD | 4 | 6 | 8 | 1 |
| VTLF | 10 | 10 | 8 | 8 |
| JNGS | 8 | 0 | 0 | 9 |
| PIGW | 7 | 10 | 10 | 10 |
| WHST | 10 | 9 | 10 | 8 |
| YLFX | 8 | 10 | 7 | 3 |
| BNGS | 10 | 10 | 6 | 4 |
| CBGS | 6 | 4 | 2 | 0 |
| CTGS | 7 | 10 | 10 | 3 |
| MNGY | 8 | 3 | 1 | 0 |

TABLE VI

Product of Example 8 Post-Emergence Injury Rating

| Plant Species | Rate Lbs./Acre | | | | | | |
|---|---|---|---|---|---|---|---|
| | 8 | 4 | 2 | 1 | 0.5 | 0.25 | 0.125 |
| WMSTD | 10 | 10 | 10 | 10(10) | 10 | 10 | 8 |
| WOAT | 10 | 10 | 10 | 10(10) | 10 | 4 | 0 |
| BDWD | 10 | 10 | 10 | 10(10) | 10 | 10 | 10 |
| BNGS | 10 | 10 | 10 | 6(10) | 10 | 10 | 1 |
| SOYB | 10 | 10 | 10 | 10(10) | 10 | 10 | 3 |
| CBGS | 10 | 10 | 10 | 0(10) | 10 | 5 | 0 |
| YLFX | 10 | 10 | 10 | 4(10) | 7 | 2 | 5 |
| JNGS | 10 | 10 | 10 | 7(10) | 10 | 5 | 2 |
| MNGY | 10 | 10 | 10 | 10(10) | 10 | 2 | 0 |
| JMWD | 10 | 10 | 10 | 10(10) | 10 | 10 | 10 |
| YNSG | 5 | 4 | 3 | 3 | — | — | — |
| PIGW | 10 | 10 | 10 | 10(10) | 10 | 10 | 10 |
| VTLF | — | — | — | 10 | 3 | 1 | 0 |
| QKGS | — | — | — | 10 | 10 | 10 | 10 |
| SPGT | — | — | — | 10 | 10 | 5 | 3 |
| CTGS | — | — | — | 7 | 6 | 4 | 1 |
| SUBT | — | — | — | 10 | 10 | 10 | 6 |
| SORG | — | — | — | 10 | 5 | 0 | 0 |
| WHT | — | — | — | 10 | 10 | 10 | 3 |
| RICE | — | — | — | 10 | 10 | 3 | 2 |
| COTN | — | — | — | 10 | 8 | 0 | 0 |
| CORN | — | — | — | 5 | 7 | 0 | 0 |
| PTBN | — | — | — | 10 | 10 | 10 | 2 |
| ALFA | — | — | — | 10 | 10 | 7 | 10 |
| OAT | — | — | — | 10 | 10 | 10 | 2 |

TABLE VII

Product of Example 12 Post-Emergence Injury Rating

| Plant Species | Rate Lbs./Acre | | | | | | |
|---|---|---|---|---|---|---|---|
| | 8 | 4 | 2 | 1 | 0.5 | 0.25 | 0.125 |
| WMSTD | 10 | 10 | 10 | 10(10) | 10 | 10 | 10 |
| WOAT | 10 | 10 | 10 | 10(10) | 10 | 10 | 4 |
| BDWD | 10 | 10 | 3 | 3(6) | 4 | 2 | 2 |
| BNGS | 10 | 10 | 10 | 7(10) | 10 | 2 | 0 |
| SOYB | 10 | 10 | 10 | 10(10) | 10 | 10 | 10 |
| CBGS | 10 | 10 | 7 | 5(9) | 6 | 3 | 2 |
| YLFX | 10 | 10 | 10 | 4(10) | 8 | 2 | 0 |
| JNGS | 10 | 10 | 10 | 6(10) | 10 | 4 | 2 |
| MNGY | 10 | 10 | 10 | 10(10) | 10 | 8 | 5 |
| JMWD | 10 | 10 | 10 | 10(10) | 10 | 10 | 10 |
| YNSG | 5 | 5 | 4 | 0 | — | — | — |
| PIGW | 10 | 10 | 10 | 10 | 10 | 10 | 10 |
| VTLF | — | — | — | 10 | 10 | 10 | 10 |
| QKGS | — | — | — | 10 | 10 | 10 | 9 |
| SPGT | — | — | — | 10 | 10 | 0 | 0 |
| CTGS | — | — | — | 10 | 5 | 0 | 0 |
| SUBT | — | — | — | 10 | 10 | 10 | 10 |
| SORG | — | — | — | 9 | 0 | 0 | 0 |
| WHT | — | — | — | 10 | 10 | 10 | 10 |
| RICE | — | — | — | 10 | 10 | 10 | 5 |
| COTN | — | — | — | 10 | 6 | 4 | 3 |
| CORN | — | — | — | 10 | 3 | 1 | 0 |
| PTBN | — | — | — | 10 | 10 | 10 | 10 |
| ALFA | — | — | — | 10 | 9 | 4 | 2 |
| OAT | — | — | — | 10 | 10 | 10 | 10 |

TABLE VIII

Product of Example 15 Post-Emergence Injury Rating

| Plant Species | Rate Lbs./Acre | | | | | |
|---|---|---|---|---|---|---|
| | 8 | 4 | 2 | 1 | 0.25 | 0.125 |
| WMSTD | 10 | 10 | 10 | 10(10) | 10 | 10 |
| WOAT | 10 | 10 | 10 | 10(10) | 10 | 3 |
| BDWD | 10 | 5 | 6 | 3(5) | 6 | 3 |
| BNGS | 10 | 10 | 10 | 6(10) | 5 | 0 |
| SOYB | 10 | 10 | 10 | 9(10) | 2 | 0 |
| CBGS | 10 | 10 | 10 | 10(10) | 9 | 10 |
| YLFX | 10 | 10 | 7 | 4(10) | 0 | 0 |
| JNGS | 10 | 10 | 10 | 10(10) | 10 | 3 |
| MNGY | 10 | 10 | 10 | 10 (10) | 10 | 8 |
| JMWD | 10 | 10 | 10 | 10(10) | 10 | 6 |
| YNSG | 9 | 7 | 5 | 0 | — | — |
| PIGW | 10 | 10 | 10 | 10 | 10 | 10 |
| VTLF | — | — | — | 10 | 0 | 0 |
| QKGS | — | — | — | 10 | 10 | 10 |
| SPGT | — | — | — | 10 | 5 | 4 |
| CTGS | — | — | — | 10 | 0 | 0 |
| SUBT | — | — | — | 10 | 10 | 10 |
| SORG | — | — | — | 10 | 0 | 0 |
| WHT | — | — | — | 10 | 10 | 6 |
| RICE | — | — | — | 10 | 10 | 2 |
| COTN | — | — | — | 10 | 0 | 0 |
| CORN | — | — | — | 10 | 0 | 0 |
| PTBN | — | — | — | 10 | 10 | 4 |
| ALFA | — | — | — | 10 | 4 | 5 |
| OAT | — | — | — | 10 | 10 | 4 |

TABLE IX

Product of Example 18 Post-Emergence Injury Rating

| Plant Species | Rate Lbs./Acre | | | | | | |
|---|---|---|---|---|---|---|---|
| | 8 | 4 | 2 | 1 | 0.5 | 0.25 | 0.125 |
| WMSTD | 10 | 10 | 10 | 10(10) | 10 | 10 | 10 |
| WOAT | 10 | 10 | 10 | 10(10) | 10 | 3 | 4 |
| BDWD | 10 | 3 | 2 | 2(2) | 2 | 0 | 0 |
| BNGS | 10 | 10 | 10 | 10(9) | 7 | 0 | 0 |
| SOYB | 10 | 10 | 10 | 10(9) | 10 | 10 | 5 |
| CBGS | 10 | 10 | 10 | 5(10) | 9 | 3 | 0 |
| YLFX | 10 | 10 | 10 | 5(10) | 6 | 1 | 0 |
| JNGS | 10 | 10 | 10 | 7(10) | 10 | 3 | 0 |
| MNGY | 10 | 10 | 10 | 8(10) | 10 | 9 | 5 |
| JMWD | 10 | 10 | 10 | 10(10) | 10 | 10 | 8 |
| YNSG | 10 | 7 | 3 | 0 | — | — | — |
| PIGW | 10 | 10 | 10 | 8(10) | 10 | 10 | 10 |
| VTLF | — | — | — | 10 | 8 | 0 | 0 |
| QKGS | — | — | — | 10 | 10 | 10 | 6 |
| SPGT | — | — | — | 5 | 3 | 0 | 0 |
| CTGS | — | — | — | 6 | 6 | 1 | 0 |
| SUBT | — | — | — | 10 | 10 | 10 | 8 |
| SORG | — | — | — | 10 | 3 | 0 | 0 |
| WHT | — | — | — | 10 | 10 | 7 | 3 |
| RICE | — | — | — | 10 | 7 | 4 | 2 |
| COTN | — | — | — | 6 | 3 | 0 | 0 |
| CORN | — | — | — | 6 | 1 | 0 | 0 |
| PTBN | — | — | — | 10 | 10 | 10 | 10 |
| ALFA | — | — | — | 8 | 5 | 2 | 0 |
| OAT | — | — | — | 10 | 10 | 4 | 1 |

TABLE X

Product of Example 32 Post-Emergence Injury Rating

| Plant Species | Rate Lbs./Acre | | | |
|---|---|---|---|---|
| | 8 | 4 | 2 | 1 |
| WMSTD | 10 | 10 | 10 | 10 |
| WOAT | 10 | 10 | 6 | 10 |
| BDWD | 8 | 3 | 3 | 0 |
| BNGS | 10 | 10 | 6 | 0 |
| SOYB | 10 | 10 | 10 | 10 |
| CBGS | 10 | 10 | 10 | 10 |
| YLFX | 10 | 10 | 6 | 3 |
| JNGS | 10 | 10 | 10 | 7 |
| MNGY | 9 | 3 | 3 | 3 |
| JMWD | 10 | 3 | 0 | 0 |
| YNSG | 3 | 3 | 0 | 0 |
| PIGW | 10 | 10 | 10 | 10 |

The abbreviations used for the plant species are as follows:

| | |
|---|---|
| ALFA | Alfalfa |
| BDWD | Bindweed |
| BNGS | Barnyardgrass |
| CBGS | Crabgrass |
| CORN | Corn |
| COTN | Cotton |
| CTGS | Cheatgrass (Downy Brome) |
| JMWD | Jimsonweed |
| JNGS | Johnsongrass |
| MNGY | Morningglory, Annual |
| OAT | Oat |
| PIGW | Pigweed |
| PTBN | Pintobean |
| QKGS | Quackgrass |
| RICE | Rice |
| SORG | Sorghum |
| SOYB | Soybean |
| SPGT | Sprangletop |
| SUBT | Sugar Beet |
| VTLF | Velvetleaf |
| WHT | Wheat |
| WMSTD | Wild Mustard |
| WOAT | Oats, Wild |
| YLFX | Foxtail, Yellow |
| YNSG | Nutsedge, Yellow |

I claim:

1. A compound of the formula $$R^1\underset{R^2}{\diagdown}N-SO_2-C\underset{S}{\overset{N-N}{\diagdown\diagup}}C-N-C-N-(CH_2)_m-C-CH\underset{Z^2-C-R^8}{\overset{Z^1-C-R^7}{\diagdown\diagup}}(CH_2)_n$$

wherein $R^1$ is lower alkyl, $R^2$ is selected from the group consisting of hydrogen and lower alkyl; or $R^1$ and $R^2$ together with the nitrogen atom form a cyclic ring structure having 4 or 5 carbon atoms and one nitrogen atom; m is the integer 0 or 1; when m is 1, $R^4$ and $R^5$ are each independently selected from the group consisting of hydrogen and lower alkyl of up to 3 carbon atoms; when m is 0, $R^4$ is hydrogen and $R^5$ is the same as defined above, $R^3$, $R^6$, $R^7$, $R^8$, $R^9$ are each independently selected from the group consisting of hydrogen and lower alkyl; n is an integer from 0 to 2; and $Z^1$ and $Z^2$ are each independently selected from the group consisting of oxygen and sulfur.

2. The compound of claim 1 which is, N-[5-(N,N-dimethylaminosulfonyl)-1,3,4-thiadiazol-2-yl]-N'-(1,3-dioxolan-2-ylmethyl)-N'-methylurea.

3. The compound of claim 1 which is N-[5-(N,N-dimethylaminosulfonyl)-1,3,4-thiadiazol-2-yl]-N'-[1,3-dioxolan-2-yl)ethyl]-N'-methylurea.

4. The compound of claim 1 which is N-[5-(N,N-dimethylaminosulfonyl)-1,3,4-thiadiazol-2-yl]-N'-(4,5-dimethyl-1,3-dioxolan-2-ylmethyl)-N'-methylurea.

5. The compound of claim 1 which is N-[5-(N,N-dimethylaminosulfonyl)-1,3,4-thiadiazol-2-yl]-N'-(4-methyl-1,3-dioxan-2-ylmethyl)-N'-methylurea.

6. The compound of claim 1 which is, N-[5-(N,N-dimethylaminosulfonyl)-1,3,4-thiadiazol-2-yl]-N'-[2,2-dimethyl-2-(1,3-dioxolan-2-yl)ethyl]-N'-methylurea.

7. The compound of claim 1 which is, N-[5-(N,N-dimethylaminosulfonyl)1,3,4-thiadiazol-2-yl]-N'-[2,2-dimethyl-2-(4-methyl-1,3-dioxolan-2-yl)ethyl]-N'-methylurea.

8. The compound of claim 1 which is, N-[5-(N,N-dimethylaminosulfonyl)-1,3,4-thiadiazol-2-yl]-N'-[2,2-dimethyl-2-(4-methyl-1,3-dioxolan-2-yl)ethyl]-N'-methylurea.

9. A herbicidal composition comprising an inert carrier and, as an essential active ingredient, in a quantity toxic to weeds, a compound of claim 1.

10. A method of controlling weeds which comprises contacting said weeds with a herbicidal composition comprising an inert carrier and, as the essential active ingredient, in a quantity toxic to weeds, a compound of claim 1.

* * * * *